United States Patent [19]

Moore, Jr. et al.

[11] 4,244,363
[45] Jan. 13, 1981

[54] DISPOSABLE ANESTHESIA CIRCUIT

[75] Inventors: Robert W. Moore, Jr., Houston, Tex.; Stanley C. Weinrich, 618 Diamondhead Blvd., Houston, Tex. 77532

[73] Assignee: Stanley C. Weinrich, Crosby, Tex.

[21] Appl. No.: 38,441

[22] Filed: May 14, 1979

Related U.S. Application Data

[63] Continuation of Ser. No. 965,081, Nov. 30, 1978, abandoned, and a continuation of Ser. No. 949,767, Oct. 10, 1978, abandoned.

[51] Int. Cl.³ ............................................. A61M 16/00
[52] U.S. Cl. ............................ 128/205.17; 128/205.24
[58] Field of Search .................... 128/203.28, 205.13, 128/205.17, 204.26, 204.25, 207.14, 207.16, 348, 349 R, 358 R, 349 BV, DIG. 9, DIG. 26, DIG. 32

[56] References Cited

U.S. PATENT DOCUMENTS

| | | | |
|---|---|---|---|
| 2,241,535 | 5/1941 | Boothby et al. | 128/205.17 |
| 2,944,546 | 7/1960 | Ziherl et al. | 128/205.17 X |
| 3,039,463 | 6/1962 | Dickey, Jr. et al. | 128/276 |
| 3,473,531 | 10/1969 | Tatham | 128/205.17 |
| 3,773,045 | 11/1973 | Boba | 128/205.13 |
| 3,796,216 | 3/1974 | Schwarz | 128/205.13 |
| 3,977,432 | 8/1976 | Vidal | 128/210 |
| 3,993,059 | 11/1976 | Sjötrand | 128/205.24 X |
| 4,002,166 | 1/1977 | Oliver | 128/204.26 |
| 4,029,093 | 6/1977 | Kohnke | 128/203.28 |
| 4,099,528 | 7/1978 | Sorenson et al. | 128/348 X |
| 4,109,651 | 8/1978 | Steigerwald | 128/205.17 |
| 4,112,940 | 9/1978 | Parkes | 128/205.13 |

*Primary Examiner*—Henry J. Recla
*Attorney, Agent, or Firm*—Ranseler O. Wyatt

[57] ABSTRACT

A breathing device employed in administering anesthetic gases to patients in a respirating system in which the exhaled gases are passed to the atmosphere rather than captured and rebreathed. The circuit herein defined is a simple, reliable and economical anesthesia circuit particularly designed for use on children and infants, and that is disposable, and that may be adjusted during use.

1 Claim, 4 Drawing Figures

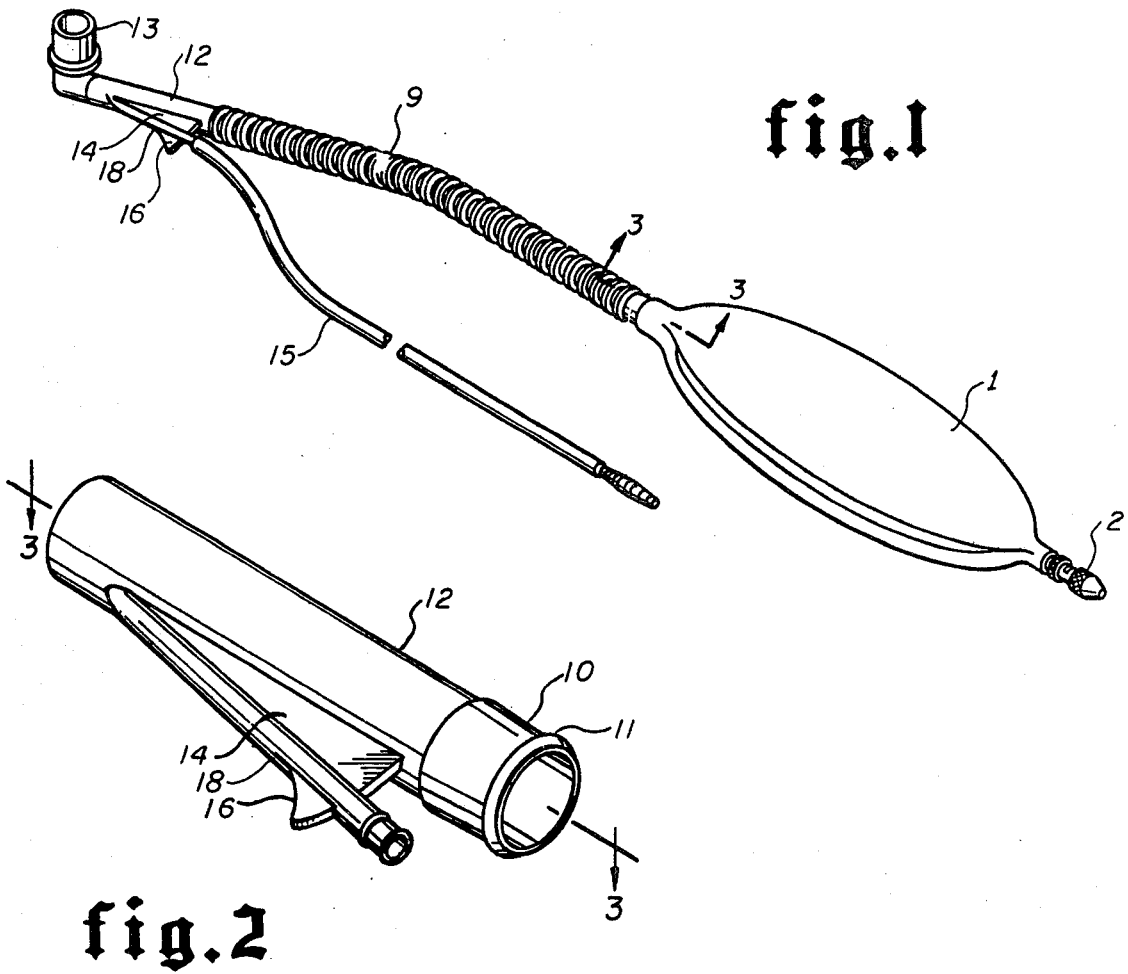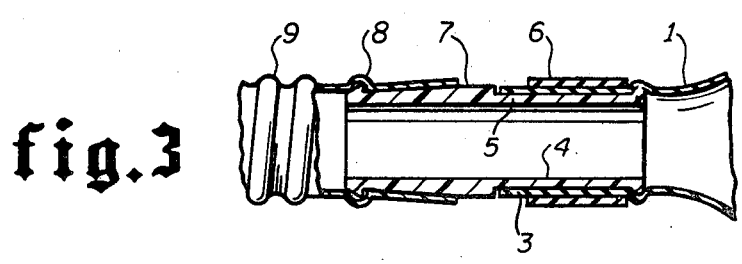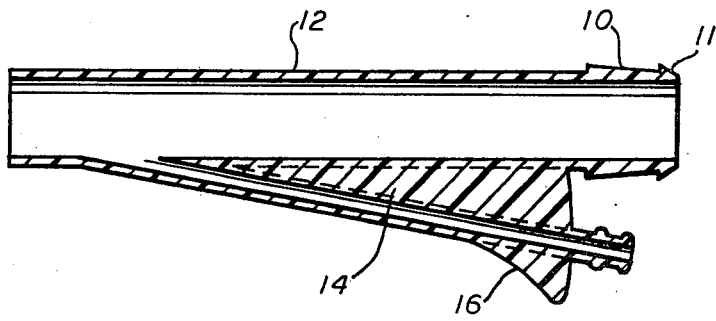

DISPOSABLE ANESTHESIA CIRCUIT

This application is in continuation of the applications filed by these applicants on Oct. 10, 1978, Ser. No. 949,767, now abandoned and Nov. 30, 1978, Ser. No. 965,081 now abandoned.

BACKGROUND OF THE INVENTION

Breathing apparatus presently in use where there is a complete muscular immobilization of the patient, and mechanical means are necessary to continue the breathing of the patient, such as during surgery, is costly, consisting of primarily stainless steel, or similar metal that may be sterilized after use, and that employ controls difficult to manipulate and incapable of fine adjustment. It is an object of this invention to provide breathing apparatus of this character that may be molded by injection molding, of a suitable polymer, and will be sufficiently low in cost that it may be economically discarded after each use, thus preventing inadvertent contamination from one patient to another, and that will be provided with novel safety means to assure a constant discharge of air and gas.

BRIEF DESCRIPTION OF THE DRAWINGS

FIG. 1 is a top perspective view of the apparatus.
FIG. 2 is a perspective view of the vortex tube.
FIG. 3 is an enlarged side elevational view, partially in cross section, of the hose-bag connection.
FIG. 4 is an elevational, cross sectional view of the juncture of the gas mixture supply conduit and the breathing bag conduit.

DESCRIPTION OF THE PREFERRED EMBODIMENTS

Figure 5:
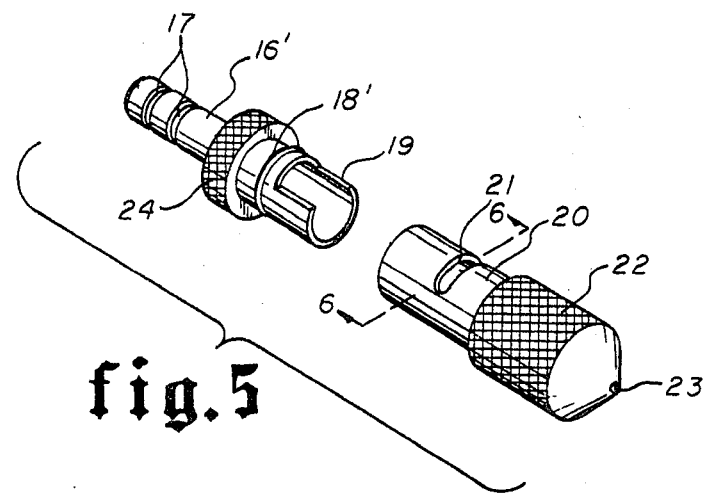
FIG. 5 is an enlarged, exploded view of the valve.
Figure 6:
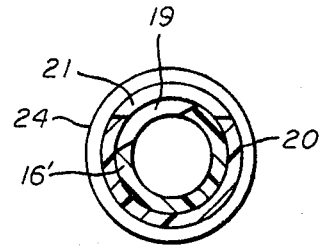
FIG. 6 is a cross sectional view, taken on the line 4—4 of FIG. 1.
Figure 7:
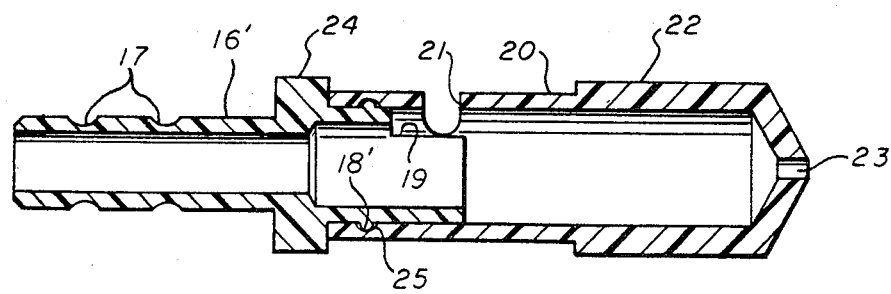
FIG. 7 is an elevational side view, in cross section, of the assembled valve.

In the drawings, the numeral 1 designates a flexible bag having the adjustable valve 2 at one end, and a neck formed at the other end into a diametrically reduced tube 3, adapted to receive the connector 4, which is a tubular member having a circumferentially reduced area adjacent one end, as 5, forming a terminal shoulder, and the reduced area extending from approximately midway the restive ends of said connector to one end, forming the neck receiving end, and the shoulder formed on the said neck receiving end assists in maintaining the bag 1 on the connector. A flexible band 6 stretched over the neck after the neck is mounted on the connector 4 further anchors the bag in position on the connector. The circumference of the connector from midway the respective ends to the opposite end is tapered as 7, to the flange 8, to receive the end of the flexible tube 9, the final corrugation receiving the flange 8.

The other end of the flexible tube 9 is received by the tapered circumference 10 and flange 11 of the junction tube 12, which is an elongated tube of rigid material, having the elbow and fitting 13 at the opposite end, adapted to receive any anesthetic breathing equipment, such as the usual mask, or an endotrachial tube (neither shown). Said junction tube 12 has an outwardly extending wing 14 which supports the air-gas mixture inlet 18, said inlet having a double flanged on its extended end to receive the hose 15 from the air-gas mixture supply (not shown). The wing 14 continues past the air-gas mixture inlet forming a finger grip 16. The junction tube assembly is intended to be formed of a suitable plastic so that it may be extruded at a minimal cost and the unit discarded after a single use to avoid possibility of contamination.

Mounted on the extended end of the breathing bag 1 is the control valve 2 having two principal components, the first being the bag receiving component 16, having a tubular connecting section in which annular grooves 17 are formed, which receives the bag, an aperture being formed in the bag for this purpose, the bag being diametrically reduced and extended forming a neck which may be stretched over the connecting section 16, and assisting in the friction seal of the bag on the valve.

An enlarged knurled area 24 is formed on the male component which serves as a grip for rotation of the components relative to each other. An annular groove 25 is formed on the inside wall of the female component in which the annular projection 25 on the male component is received. An elongated slot 19 is formed in said male component and the portion of the male component extending from the knurled area 24 to the slotted end is telescopically received by the female component 20. A transverse elongated slot 21 is formed in the female component 20, and substantially half of the length of the said female component is enlarged from a point adjacent said slot to the extended end of said female component, and knurled, as at 22, to provide a grip for rotation of the part. A small passageway is formed in the extended end of said female component, as at 23, to provide a constant relief port, as a safety measure, for said valve. When the parts are assembled, the connection with the bag, and the ring 24, will provide a secure seal to insure against leakage, and yet will provide easy rotation of the components relative to each other, for adjustment of the flow through the openings 19-21.

In use, the hose 15 is attached to a gas supply, and the anesthetic attachment is secured to the elbow 13. The bag 1 will quickly fill, and the apparatus is ready for use. The user will adjust the valve 2 by rotating the female component relative to the male component until the desired escape space is provided. This provides a non-rebreathing inhalator, permiting the exhaled gases to pass to the atmosphere, rather than be reinhaled. The user controls the pressure of the gas mixture to the patient by pressing on the bag 1. Where the patient has been muscularly immobilized, it is necessary to mechanically perform the breathing operation for the patient. The gas flows into the mask and inflates the air bag, and will quickly fill both, and the inlet valve 2 is set for the desired amount of air to be admitted into the bag, and gas will flow to the patient in increased amounts as the pressure is applied to the bag 1 by squeezing same, and the used air and gas will be exhausted through the valve 2 as the pressure on the bag 1 is released. The rotation of the female component of the valve 2 relative to the male component may be done with one hand, leaving the other hand free for such work as may be necessary. The safety element of the aperature 23 assures sufficient relief to prevent overinflation of the patient's lungs in case the relief valve is adjusted full-closed purposefully, to sigh a patient, or is inadvertently closed. When the device is used in conjunction with anesthesia apparatus employing endotracheal equipment, the circuit can be left hooked to the patient with an oxygen supply for recovery, thus offering the advantage of easy monitoring of breathing progress and also allowing for fast and simple assisted respiration should the patient require it while in recovery from anesthetics.

The valve 2 functions as a flow control of the anesthesia circuit. This is achieved by exhaust regulation through the adjustable orifice 21. Closing the orifice, or adjusting it to a smaller opening by rotation of the female component relative to the male component, inhibits exhaust, thereby increasing pressure to the patient when the breathing bag 1 is squeezed by the anesthetist. Conversely, adjusting the valve so that a greater opening is provided, allows increased exhaust and a reduction of pressure to the patient.

What we claim is:

1. In a disposable anesthesia circuit, a flexible breathing bag, a rigid tube having one end connected to said bag in flow relation therewith and a gas-air mixture inlet housing having a passageway extending into said tube, a hose mounted on said inlet housing communicating with said passageway and adapted to be connected to a source of supply of gas-air mixture and adapter means connected to the other end of said tube for connection to a patient an adjustable exhaust valve mounted in said bag, said valve having a male and a female component, each component having an enlarged knurled portion for rotation of said components relative to each other, said male component having a longitudinal slot, and said female portion having a transverse elongated slot, the exposed slot area of the male member increasing as the female member is rotated in one direction on said male member and descreased when said female member is rotated in the other direction and said female component having an escape passageway in the extended end thereof.

* * * * *